US006003513A

United States Patent [19]

Readey et al.

[11] Patent Number: 6,003,513

[45] Date of Patent: Dec. 21, 1999

[54] REBREATHER HAVING COUNTERLUNG AND A STEPPER-MOTOR CONTROLLED VARIABLE FLOW RATE VALVE

[75] Inventors: Peter Francis Readey; Michael J. Cochran, both of Plano, Tex.

[73] Assignee: Cochran Consulting, Richardson, Tex.

[21] Appl. No.: 08/590,693

[22] Filed: Jan. 12, 1996

Related U.S. Application Data

[63] Continuation-in-part of application No. PCT/IB95/00396, May 15, 1995.

[51] Int. Cl.[6] .......... A61M 16/00; A62B 9/02; A62B 7/04; F16K 31/26

[52] U.S. Cl. .......... 128/205.24; 128/205.23; 128/204.26; 128/205.28; 128/204.28; 128/205.17; 128/202.22

[58] Field of Search .......... 128/202.22, 205.28, 128/205.24, 205.23, 204.26, 204.28, 205.17, 201.27, 201.28, 204.18, 204.21, 204.22, 204.29, 205.11, 205.12, 205.13, 205.22

[56] References Cited

U.S. PATENT DOCUMENTS

| | | | |
|---|---|---|---|
| 3,252,458 | 5/1966 | Krasberg | 128/202.22 |
| 3,556,098 | 1/1971 | Kanwisher et al. | 128/202.22 |
| 3,788,310 | 1/1974 | Fleischmann | 128/205.12 |
| 3,794,021 | 2/1974 | Lambertsen | 128/204.28 |
| 3,827,432 | 8/1974 | Lundgren et al. | 128/204.29 |
| 3,951,137 | 4/1976 | Coukle . | |
| 4,192,001 | 3/1980 | Villa | 364/418 |
| 4,313,743 | 2/1982 | Wallace | 128/202.22 |
| 4,350,662 | 9/1982 | Dowgul et al. . | |
| 4,423,723 | 1/1984 | Winkler et al. | 128/204.22 |
| 4,440,162 | 4/1984 | Sewell et al. | 128/202.22 |
| 4,454,878 | 6/1984 | Morrison | 128/201.27 |
| 4,563,758 | 1/1986 | Paternostro | 367/132 |
| 4,586,136 | 4/1986 | Lewis | 364/418 |
| 4,658,358 | 4/1987 | Leach et al. | 364/418 |
| 4,791,922 | 12/1988 | Lindsay-Scott | 128/205.28 |
| 4,882,678 | 11/1989 | Hollis et al. | 364/413.31 |
| 4,939,647 | 7/1990 | Clough et al. | 128/205.28 |
| 4,964,404 | 10/1990 | Stone | 128/204.22 |
| 4,970,897 | 11/1990 | Budinger | 73/432.1 |
| 4,999,606 | 3/1991 | Comerford et al. | 340/525 |
| 5,031,160 | 7/1991 | Koizumi et al. | 368/10 |
| 5,033,818 | 7/1991 | Barr | 350/174 |
| 5,036,841 | 8/1991 | Hamilton . | |
| 5,103,685 | 4/1992 | Wright | 73/865.1 |
| 5,148,376 | 9/1992 | Sato | 364/558 |
| 5,189,646 | 2/1993 | Sako et al. | 368/10 |

FOREIGN PATENT DOCUMENTS

| | | |
|---|---|---|
| 0 182 581 | 5/1986 | European Pat. Off. . |
| 0 439 255 | 7/1991 | European Pat. Off. . |
| WO 95/31367 | 11/1995 | WIPO . |

OTHER PUBLICATIONS

*The International Dictionary of Physics and Electronics,* D. Van Nostrand Co, Inc., copyright 1956, pp. 703–704.

*Primary Examiner*—Kimberly L. Asher

*Attorney, Agent, or Firm*—Gregory M. Howison; Mark W. Handley

[57] ABSTRACT

A re-breather that includes an inhalant counterlung (18) and an exhalant counterlung (20), with a mouthpiece (30) disposed therebetween. Gas flows from the counterlung (18) to the mouthpiece (30) for use by the diver, with exhalant from the diver directed to the counterlung (20). Gas forced out of the counterlung (20) is input to a canister/scrubber (10) for processing through a scrubbing material in an interior canister (14). The $CO_2$-depleted gas is passed back to the counterlung (18). The counterlung (18) has disposed therein a $PPO_2$ sensor (68) which is directed toward a control system (66) for controlling a valve (46) to adjust the rate of flow of oxygen from a bottle (40) into the $CO_2$-depleted gas exiting the canister/scrubber 10 prior to input to the counterlung (18). The rate is varied to maintain the $PPO_2$ level at a substantially constant level.

20 Claims, 7 Drawing Sheets

REBREATHER HAVING COUNTERLUNG AND A STEPPER-MOTOR CONTROLLED VARIABLE FLOW RATE VALVE

CROSS REFERENCE TO RELATED APPLICATIONS

This Application is a Continuation-in-Part of pending PCT Application No. IB 95/00396, filed May 15, 1995 entitled "Breathing Apparatus" and was published on Nov. 23, 1995, International Publication No. W095/31367, which claims priority in Great Britain Patent Application Ser. No. 9409683.1, filed May 24, 1994, designating the United States.

TECHNICAL FIELD OF THE INVENTION

The present invention relates in general to breathing apparatus and, more particularly, to an underwater breathing apparatus with a re-breathing capability.

BACKGROUND OF THE INVENTION

Breathing apparatus for use in an underwater diving situation in atmospheres unsuitable for sustaining life have been utilized in numerous applications. These systems provide the gas supply system for a user when operating in an unsuitable environment. They are typically portable and accommodate for various adverse conditions in the unsuitable atmosphere.

In underwater diving environments, it is necessary to not only provide a source of breathing gas, but also account for the high pressures in the environment, as these breathing apparatus are utilized at various depths. As the depth increases, the environment becomes more hazardous and more care should be taken.

In conventional diving apparatus, the diver determines his "dive profile" and will mix the gases in his breathing apparatus to provide the proper gas mixtures at the desired depth, this being a well-documented procedure. Additionally, dive computers are provided for allowing the diver to monitor his dive profile, such that ascent and descent times can be monitored to insure that the diver does not develop a case of the "bends" or other well-known side effects of deep dives. However, conventional apparatus with gas mixtures provide only a minimal amount of time on the bottom, due to the fact that only a finite amount of gas can be carried with the diver. These types of systems vent the gas that is breathed into the lungs and then exhaled. Unfortunately, these types of systems allow a large amount of unmetabolized oxygen to be vented into the water.

Another type of apparatus, a re-breathing apparatus, has been developed to recycle the exhaled gas to remove carbon dioxide therefrom with a "scrubber" and then recycle the unmetabolized oxygen. Oxygen or Oxygen-enriched gas is then injected into the "scrubbed" gas to maintain the partial pressure of oxygen in the gas at a desired level, and then the mixture is passed back to the user for re-breathing. One such system is described in Great Britain Patent Application Ser. No. 9409683.1, filed May 24, 1984, upon which PCT Application No. IB 95/00396, filed May 15, 1995, was based. This is entitled "Breathing Apparatus" and was published on Nov. 23, 1995, as International Publication No. W095/31367, which application is incorporated herein by reference.

Developers of re-breather systems design the systems to maintain high efficiency, and minimize weight with concurrent minimum effort expended by the user in breathing during use of the system. Early re-breather systems were relegated to use by professionals in unsafe environmental conditions, such as diving or firefighting due to the complexity and costs of the systems, in addition to the extensive training required for the use of these systems. Although the systems are relatively simple in construction since pure oxygen is utilized, the early systems were undesirable due to the problem of oxygen toxicity, i.e., if the partial pressure of oxygen ($PPO_2$) rises, or falls, this can be detrimental to the diver.

There are two types of re-breather systems, a closed circuit system and a semi-closed circuit system. The semi-closed circuit system is one wherein the diver is allowed to adjust the flow of oxygen-enriched gas into the breathing loop with the aid of either a calculated $PPO_2$ or measured liters per minute. This is effected through some type of manual valve. Alternatively, the diver can have this preset at the surface, this typically being the case, wherein the diver will know the depth that the system is to be operated and it is permanently set at the surface. This, in the past, has been viewed as an advisable way to operate a re-breather, wherein the user cannot inadvertently manipulate the controls to increase or decrease the $PPO_2$. This is quite acceptable when working at constant depths; however, when depths are varying, the oxygen must be varied and the user in a semi-closed circuit system must have some ability to change the amount of oxygen that flows into the breathing side of the system.

In closed circuit systems, a feedback mechanism is provided wherein the $PPO_2$ is monitored and a valve is opened and closed to adjust the amount of oxygen that is introduced to the breathing side of the apparatus. These systems have typically utilized pulse-type valves, which are fully open or fully closed. These systems have a disadvantage in that, when the valve is open, the full pressure of oxygen is introduced into the breathing side of the apparatus, resulting in an uneven regulation of oxygen. Alternatively, if the system fails, it either fails open or it fails closed. If it fails open, this can be disastrous whereas, if it fails closed, this merely requires some type of backup.

SUMMARY OF THE INVENTION

The present invention disclosed and claimed herein comprises a breathing apparatus. The apparatus includes an inhalant counterlung, having an inlet hose for receiving $CO_2$-depleted gas and an outlet hose for outputting breathing gas. A breathing mouthpiece is provided for allowing a diver to inhale and exhale therethrough. The mouthpiece has an inlet through a first one-way valve which is connected to the outlet of the inhalant counterlung. The mouthpiece also has an outlet for allowing gas to be exhaled through a separate one-way valve for expelling exhaled gas. A $CO_2$ scrubber canister is provided for receiving the output of the mouthpiece, removing the $CO_2$ therefrom, and outputting $CO_2$-depleted gas to the inhalant counterlung. An $O_2$ source is provided in a tank, which is then input to a variable flow rate, constant velocity valve to the interior of the inhalant counterlung. The valve is operable to set the flow rate at a predetermined and constant flow rate at a constant velocity. A $PPO_2$ sensor is provided for sensing the pressure of oxygen in the counterlung. A drive control for a control system then sets the valve to a predetermined flow rate as a function of the $PPO_2$ level, such that the $PPO_2$ level is maintained substantially constant within the inhalant counterlung.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

Figure 1:
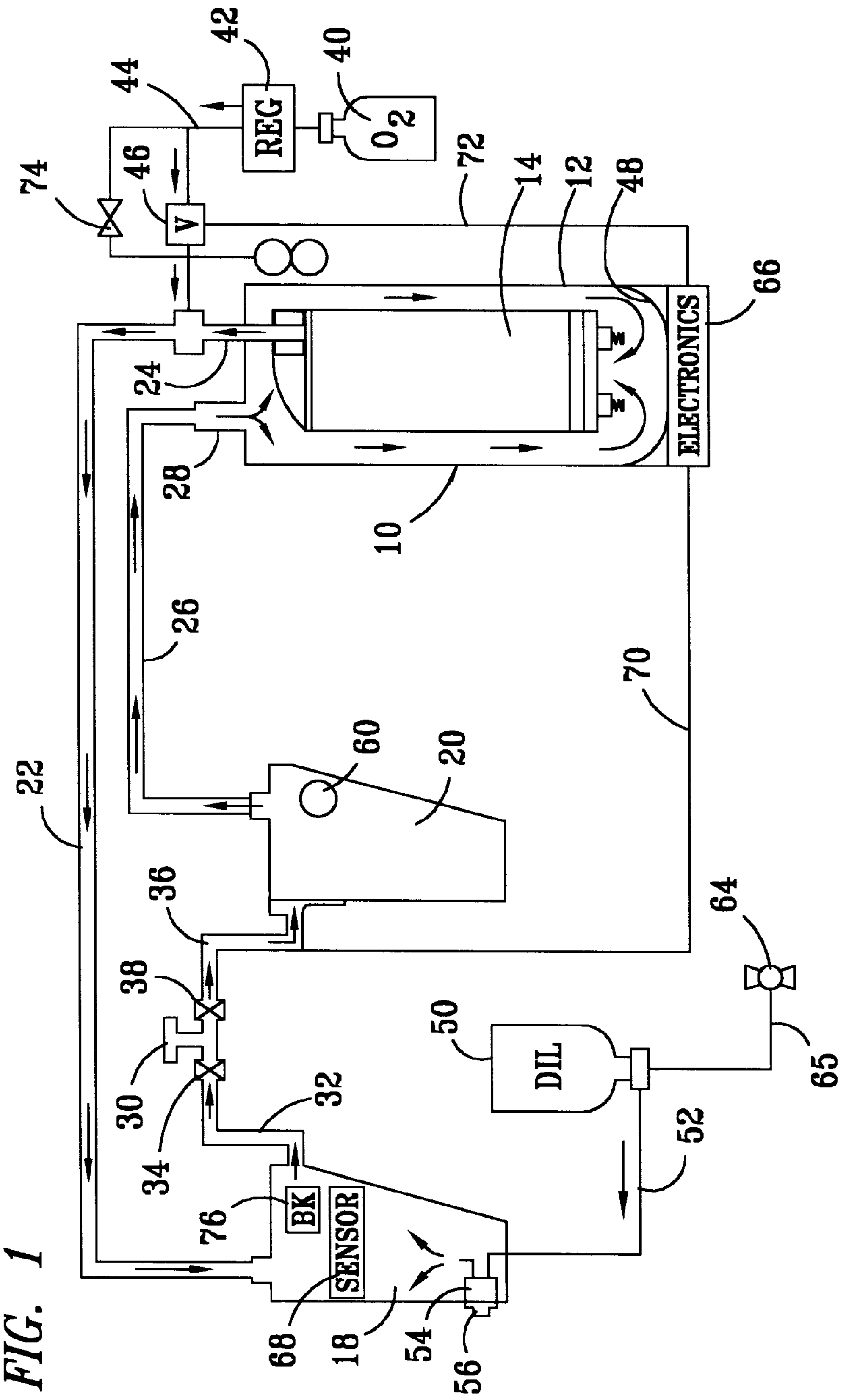
FIG. 1 illustrates an overall diagrammatic view of the system of the present invention.

Referring now to FIG. 1, there is illustrated a diagrammatic view of the breathing apparatus of the present invention. The breathing apparatus is a re-breather. In a re-breather, gas is recirculated through a canister/scrubber 10, which in this embodiment consists of an outer canister 12 and an inner canister 14, which inner canister 14 includes the $CO_2$ absorbent material. The canister/scrubber 10 is interfaced with two “counterlungs” an inhalant counterlung 18 and an exhalent counterlung 20. The counterlungs 18 and 20 are operable to provide for a capacity approximating that of a full human lung such that, when the diver exhales, the full amount of exhalation gas is contained easily within the counterlung 20 and the amount of gas contained in the counterlung 18 can be drawn into the lungs when inhaling. This configuration is referred to as a dual counterlung configuration, wherein each of the counterlungs 18 and 20 are sited on the harness on the diver’s shoulders and chest. This is similar to the U.S. Navy MK6 and was chosen to aid gas flow and diver comfort. This “shoulder/chest” position is well known to be the most advantageous position for use, reducing user fatigue caused by uncomfortable side effects of hydrostatic pressures. On occasion, the user can carry a redundant set of counterlungs due to certain mission requirements or to increase performance.

The inhalation counterlung bag 18 is connected through a hose 22 to an outlet port 24 on the canister/scrubber 10. The exhalation counterlung 20 is connected to a hose 26 to an inlet port 28 on the canister/scrubber 10. Additionally, the inhalation counterlung 18 is connected to one side of a mouthpiece 30 through a hose 32 and a one-way valve 34. The exhalation counterlung 20 is connected to the mouthpiece 30 through a hose 36 and a one-way valve 38. Therefore, when the diver breathes through the mouthpiece 30, a decrease of pressure in the mouthpiece 30 will cause gas to pass through hose 32 and through valve 34 and, an increase in pressure will cause valve 34 to close and valve 38 to open and allow exhaled gas to pass to exhalation counterlung 20.

An oxygen bottle 40 is provided which is operable to contain $O_2$ or $O_2$-enriched gas. This is contained at a relatively high pressure of 300 bar, which is regulated down by a regulator 42 to a pressure of 400 psi in a hose 44. This is input to a motor control valve 46, which motor control valve 46 will be described hereinbelow. However, motor control valve 46 is controlled by a brushless DC stepper motor to control the flow rate therethrough, which flow rate is a “constant” flow rate. This is then input to the outlet port 24 and the hose 22 to allow oxygen to be introduced from the bottle 40 to the hose 22 at a substantially constant flow rate. The system can operate as a closed circuit constant $PPO_2$ system with the gas mixture in the bottle being oxygen or oxygen enriched gas. If the gas is Nitrox or Trimix, the system can then be operated as a semi-closed $PPO_2$ or semi-closed constant percentage system.

The inner canister 14 is the canister that contains the scrubber material. Gas is passed through the inlet port 28 from the exhalation lung 20 down to the bottom of the outer canister 12 and then passes around the lower surface 48 thereof, which is dish-shaped and then is directed up through the bottom of the inner canister 14 and into the scrubbing material. The gas passes through the scrubbing material up to the outlet port 24, by which time the $CO_2$ is removed and the unmetabolized oxygen that was output from the exhalation counterlung 20 is then passed back to the inhalation counterlung 18. The operation of the gas moving through the canister 14 is generally as described in PCT Application WO95/31367, entitled “Breathing Apparatus,” filed May 14, 1995, and published Nov. 23, 1995, which reference is incorporated herein by reference.

During a dive from the surface to a deeper depth, the pressure will increase. At the surface, the inhalation counterlung 18 can be inflated with a separate diluent tank 50. The diluent tank 50 is connected through an L. P. gas hose 52 through the interior of the inhalation counterlung 18 through a valve 54. The valve 54 is a valve that is operated by two methods, manually or by pressure. The diver can depress an external diaphragm on an exterior portion 56 of the valve 54 which extends to the exterior of the inhalation counterlung 18, or the water pressure will cause the diaphragm in the exterior portion 56 to be depressed. The purpose of this is to maintain inflation of the inhalation counterlung 18. The mixture of the diluent gas in a diluent container 50 is determined by the diver, depending upon the desired dive profile. If the diluent gas in the tank 50 were not provided, then the increasing pressure as the diver descended, would cause the inhalation counterlung 18 to deflate. Of course, it cannot be inflated from the oxygen bottle 40. Therefore, the diver can either depress the diaphragm on the valve 54 to increase the pressure within the inhalation counterlung 18 or, alternatively, the increasing pressure exterior to the counterlung 18 will cause the diaphragm of valve 54 to be depressed and allow gas to flow from the diluent bottle 50 to the interior of the inhalant counterlung 18. The contents of the diluent container 50 are well known and selected by the diver for his particular diving profile and the depth at which he intends to dive.

For the purpose of making an ascent, the exhalant counterlung 20 has associated therewith a depressurization valve 60 which allows the diver to select a setting to decrease the pressure in the exhalant counterlung 20. For example, when the diver makes an ascent, the decreasing pressure will result in an increase of pressure in both the inhalant counterlung 18 and the exhalant counterlung 20. The diver can purge this to the exterior with the valve 60. (Overpressuring of the system will also purge accumulated water from the system/ canister/ scrubber 10). Should the canister fail, then by presetting this exhaust valve 60, it is possible to bypass the canister 10 and double the duration of carried gas by using the loop as an open circuit SCUBA system.

The diluent tank 50 is provided with a mouthpiece 64 connected to the bottle 50 through the hose 65. This can be used in an emergency situation for the diver, if necessary, and totally bypass the re-breathing apparatus.

The control system for the breathing apparatus of the present invention is provided via an enclosed electronics module 66 contained in the bottom of the outer canister 12. These electronics are interfaced with various sensors and provide various control outputs. The sensors that are provided are $PPO_2$ sensors and $CO_2$ sensors in a sensor block 68, which are contained within the inhalant counterlung 18. These sensors are connected via a wire to cable 70 to the electronics module 66. The electronics module 66 then communicates with a wrist system having a display. This communication is effected through a wireless link. This control system is the prior art system and is described in U.S. patent application Ser. No. 08/578,157 filed Dec. 29, 1995 (Atty. Dkt. No. COCH-23,710), a Continuation-in-part of U.S. application Ser. No. 08/514,363, filed Aug. 11, 1995, now U.S. Pat. No. 5,617,848, which is a Continuation of U.S. patent application Ser. No. 08/154,022, filed Nov. 17, 1993 which is incorporated herein by reference. The electronics module 66 also provides a drive control signal on a line 72 to control the valve 46.

The system operates in a closed circuit configuration such that the $PPO_2$ in the inhalant counterlung 18 is sensed and, if too high, the flow of oxygen is decreased to valve 46 and, if too low, the valve 46 is opened to increase the flow. If it were to fail, the flow would not be interrupted; rather, it would be maintained at its constant rate. However, the user may wish to operate in a semi-closed circuit condition, wherein the user could, via observing the output of the $PPO_2$ detected by the sensor on the wrist display (not shown), adjust the $PPO_2$ level through a manual valve 74 that bypasses the automatic valve 46. The user could also manually abort to this semi-closed circuit condition.

In the event that the electronics in the electronics module 66 fail and/or the sensors in sensor block 68 fail and/or the valve 46 fails, there is provided a backup system 76 disposed within the inhalant counterlung 18. The backup 76 includes a self-contained set of $PPO_2$ sensors and $CO_2$ sensors, separate from the sensors in the sensor block 68 and also provides a self-contained battery and electronics module to sense the values of the $PPO_2$ sensor, to provide the necessary calculations and then transmit these to a separate wrist unit (not shown) from the electronics module 66. This is a separate "dive computer" that calculates true on-line decompression based upon the actual gas breathed. With the use of this backup system 76 and the manual valve 74, the diver can continue virtually uninterrupted, it being noted that the flow remains constant at the last setting of the valve 46 (when the valve 46 is not the reason for the failure). This backup system 76 is a system that automatically operates when a certain pressure is achieved to indicate the diver has left the surface, and recognizes and stores the profile of the dive and can then be utilized by the diver in an ascent. Should the sensors on this $PPO_2$ redundant system 76 fail, the backup dive computer will serve as a "standard dive computer", i.e., it will calculate the necessary breathing parameters for the user with no information as to the $PPO_2$ levels. It will utilize the last known data received and will abort to either a default setting or a pre-programmed abort plan.

Figure 2:
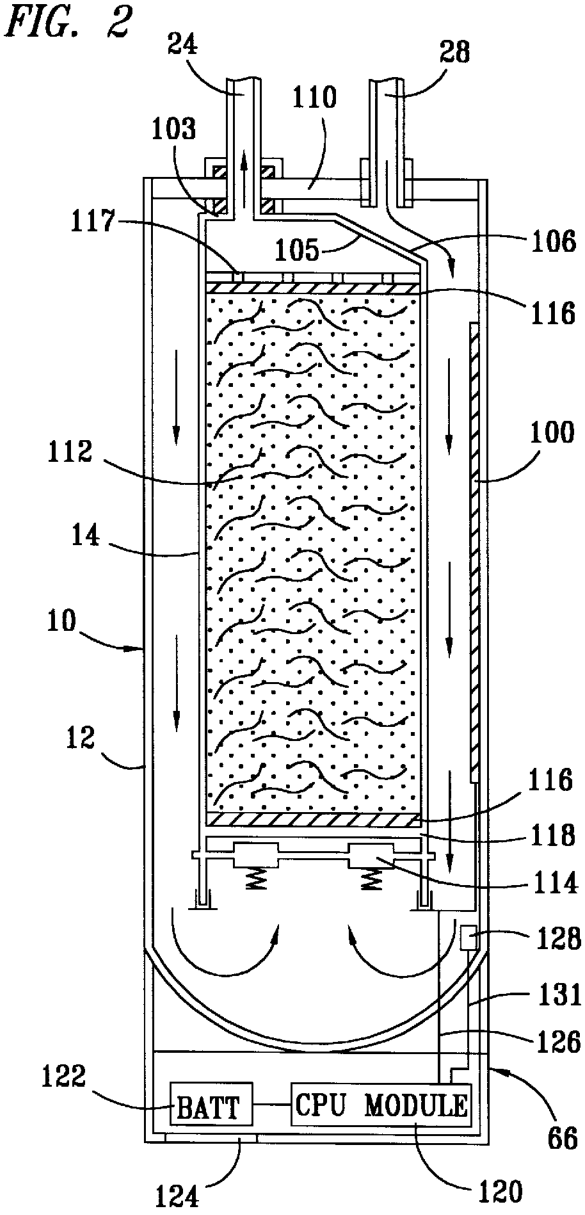
FIG. 2 illustrates a sectional view of the re-breathing canister.

Referring now to FIG. 2, there is illustrated a detail of the canister/scrubber 10. The outer canister 12 is manufactured of black polyethylene or like material to aid in insulation and ultraviolet light radiation resistance. The outer canister 12 on the interior thereof contains a temperature strip 100, which is a thin straw of gel with a plurality of thermistors disposed along the length thereof, four thermistors in the preferred embodiment, which are disposed at regular intervals along the length of the probe 100. As will be described hereinbelow, temperature data received from the temperature probe 100 is passed through a waterproof fitting at the bottom of the outer canister 10 to the electronics module 66.

At the top of the outer canister 12 is disposed a see-through plate 110, which has a diameter less than that of the outer canister 12 and is operable to be disposed in an insertable manner into one end of the outer canister 12. The see-through plate 110 and outer canister 12 are removable to allow access to the inner canister 14. The inner canister 14 is slidingly connected to the plate 110, such that it can be removed as a module and then disassembled. Additionally, the see-through plate 110, when the system is deployed underwater, allows the diver to check for excessive moisture in the loop at the surface or in the water, with a buddy to check for flooding or water ingress. Anything other than a fine mist of condensation is unacceptable and the diver would be advised to empty or change the pre-pack, depending on the level of saturation. The window 110 is held in place by a clamp and O-rings seal mechanism (not shown).

The inner canister 14 is fabricated from material that is reflective to heat, and utilizes this reflective nature to assist in the efficient use of absorbent material 112 that is disposed in the inner canister 14. The upper end of the inner canister 14 has a shape on one side thereof that is tilted, this being a surface 106. This surface is tilted at a position beneath the inlet valve 28 and slightly offset from the vertical center of the outer canister 12 to aid, by a venturi effect, the flow of gas around the system. The absorbent material 112 is a pre-pack of absorbent that is slid into the inner canister 14 every four hours of use time. The inner canister 14 is held away from the outer walls of the outer canister 12, such that small amounts of water that may ingress into the system will, when the diver inverts, run along the outer canister walls instead of entering the inner canister.

The pre-packed absorbent packs of absorbent material 112 are delivered in foil wrap to prevent degradation of material and expand shelf life. The packs are user replaceable. When changing the pack, the user will remove the inner housing and plate 110 and a restraining spring-loaded spider mechanism 114 can be released and the absorbent pack with the absorbent material 112 slid out the bottom of the inner container 14. The absorbent material 112 is held between two filter elements 116, typically of an open celled foam type material, disposed at both ends of the absorbent material 112, which filter elements act as dust traps. A gas-permeable membrane 118 is disposed on the exterior side of the filter 116 at the lower end of the inner canister 14 with none disposed at the opposite end. The opposite end has a perforated spacer plate 117 disposed exterior to the filter 116 to provide a support surface therefor. The gas-permeable 118 membrane is made of a material such as VYON®, that allows gas, but not exhaled, saturated vapor to pass therethrough. Additionally, this membrane 118 warns the diver of any water ingress into the system by increasing the breathing resistance on the unit as it reaches the saturation point. If the diver continues to utilize the system without taking appropriate action, the unit will eventually reach a point where the diver cannot re-breathe gas through the loop and is forced to use the bail-out mode. This membrane 118 and its effect on the breathing resistance was designed to alert the diver to any hazards and have them abort or take appropriate action, rather than to allow caustic materials to be ingested into the lungs. At the top of the inner canister 14 a metal spacer plate 103 is disposed that creates a collection chamber 105 at the top of the metal inner canister 14 before the gas retrieval to the inhalant counterlung 18 (shown in FIG. 1). This metal spacer 103 provides a base for the dust filters and absorbents, and is suitably perforated to aid gas flow and reduce breathing resistance.

The electronics module 66 contains a CPU module 120 and batteries 122. The batteries are accessible through an opening 124 on the canister base that is O-ring sealed. The electronics module 66 has the exterior surface thereof manufactured from DELRIN®, or other appropriate material depending on the depth rating for its intended limit. It is operable to be separated from the main portion of canister 12 to protect it against flooding and contaminants. The CPU module 120 is interfaced with the temperature probe 100 (AB) via a wire 126. Additionally, a water detector 128 is provided in the interior of the exterior housing 12. This water detector 128 is essentially two contacts separated by an air gap, which the CPU module 120 then measures the resistance therebetween. If salt water enters the system and is at such a level that the two contacts will be bridged, the resistance will decrease sufficiently that this indicates flooding of the system. The system will indicate a "flood" condition which can be indicated to the diver. This water detector 128 is connected to the CPU module 120 via a line 131. The lower portion of the canister 14 is hemispherically shaped for aerodynamic purposes.

Figure 2A:
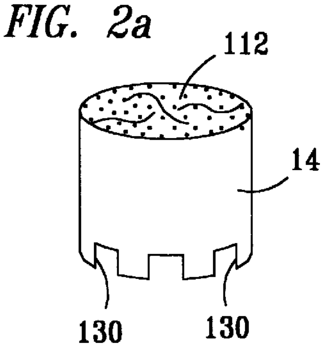
FIG. 2*a* illustrates a partial cut-away, perspective view of the design of the inner canister on the bottom edge thereof.

Referring now to FIG. 2*a*, there is illustrated a detail of the lower edge of the inner canister 14, which illustrates a plurality of openings 130 disposed along the lower peripheral edge thereof. These openings 130 allow gas to pass therethrough, thereby decreasing the resistance to breathing.

Figure 3:
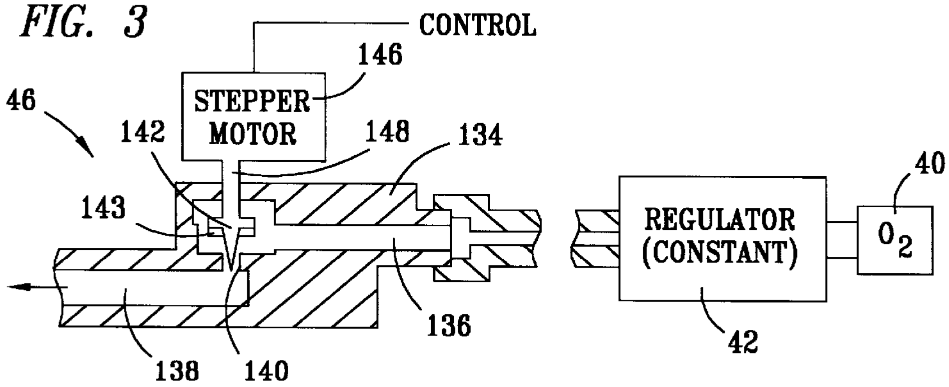
FIG. 3 illustrates a cross-sectional view of the oxygen supply valve and the stepper motor.

Referring now to FIG. 3, there is illustrated a cross-sectional view of the valve 46. The valve 46 is a needle valve which is comprised of a housing 134 having an inlet chamber 136 and an outlet chamber 138, which are connected together through an orifice 140. The orifice 140 is disposed such that a needle valve 142 can be positioned thereover and pass through the orifice 140. The orifice 140 has parallel vertical walls as compared to the needle valve 142 which has tapered walls. As needle valve 142 is inserted into the orifice 140, the surface area of the orifice 140 decreases, thus increasing resistance to flow and decreasing the flow rate. The needle 142 has a collar at the upper end thereof extending outward with a flat lower surface. The flat lower surface has a sealing layer 143 disposed thereon, which will contact the peripheral edges of the orifice 140 to provide a seal. This seal results in a positive shut-off valve operation.

The pressure within the housing chamber 136 is maintained at a constant pressure via the regulator 42. The regulator 42 is a regulator that is not subject to external hydrostatic forces. It therefore is not in communication with the exterior environment. It regulates the pressure within the $O_2$ bottle 40 at a pressure of approximately 300 bar down to a pressure of 400 psi with the assistance of the valve 46. Essentially, there is a pressure drop across the valve which is approximately a factor of 2.2. Therefore, the pressure in the chamber 136 is approximately 2.2 times the pressure in the chamber 138. Since the pressures are maintained to an accurate level, this results in a constant flow through the orifice 40.

A stepper motor 146 is provided for controlling the needle valve 142. The stepper motor is operable to increment a rotating shaft 148, merely by providing pulses to the stepper motor 146. This is a "brushless" DC motor. The purpose for providing a brushless motor is due to the fact that the system operates in a high oxygen content environment. If sparks from brushes in a conventional rotating motor were present, this could result in danger to the operator of the system.

Figure 4:
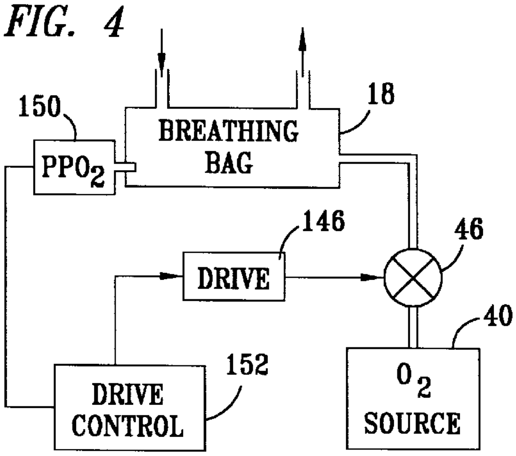
FIG. 4 illustrates a schematic view of the feedback circuit.

Referring now to FIG. 4, there is illustrated a diagrammatic view of the feedback mechanism. The oxygen or high oxygen percentage from the $O_2$ bottle 40 is metered to the inhalant counterlung 18 with the valve 46. A $PPO_2$ sensor 150 is provided in communication with the interior of the counterlung 18. The $PPO_2$ sensor 150 is input to a drive control mechanism 152, which is operable to control the driver 146 to either open the valve 46 or close the valve 46 by an incremental amount. If the $PPO_2$ is determined to have increased, the drive 146 will slightly close the valve 46 and, if the $PPO_2$ level has decreased, the drive control 152 will control the stepper drive motor 146 to slightly open the valve 46. Additionally, if there is a significant decrease in the $PPO_2$, the drive control 152 can determine the amount of incrementing that is required to further open the valve 46. Further, the speed at which it closes can also be determined. This is essentially a negative feedback system for a closed circuit. This is totally independent of pressure and the diver. It is literally dependent upon the setting that the diver initially placed into the system to determine what the $PPO_2$ is to be. Once at a given pressure or depth, the diluent bottle 50 could be turned off and the gas continually recycled with oxygen added to maintain the $PPO_2$ level.

Figure 5:
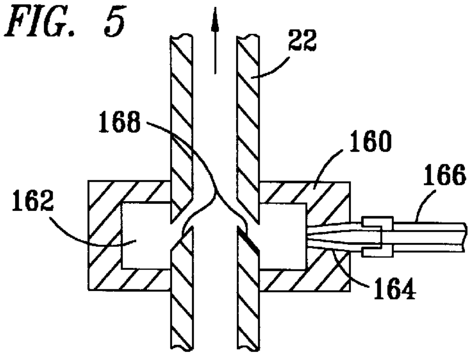
FIG. 5 illustrates a cross-sectional view of the oxygen inlet orifice.

Referring now to FIG. 5, there is illustrated a cross-sectional view of an input orifice for interfacing the hose 22 with the valve 46 (shown in FIGS. 1 and 3). A collar 160 is disposed about a predefined section of the hose 22 proximate to the outlet 24 (shown in FIG. 1). This collar 160 is annular and has disposed therein an annular chamber 162. The annular chamber 162 is disposed proximate the exterior surface of the hose 22. A fitting 164 is disposed to the exterior of the collar 160 communicating with the chamber 162. The fitting 164 is hollow, such that it can interface with the hose 166 which is an input to the valve 46 to allow oxygen to be carried therethrough. There are disposed outward slanted orifices 168 in the walls of the hose 22. These orifices 168 are slanted through the walls of the hose 22 in the direction of the gas flow. Therefore, as the gas passes the orifices 168, a venturi effect is provided. It should be understood that the hose 22 comprises both flexible and a fixed conduit, there only being one hose 22 illustrated for simplicity.

Figure 6:
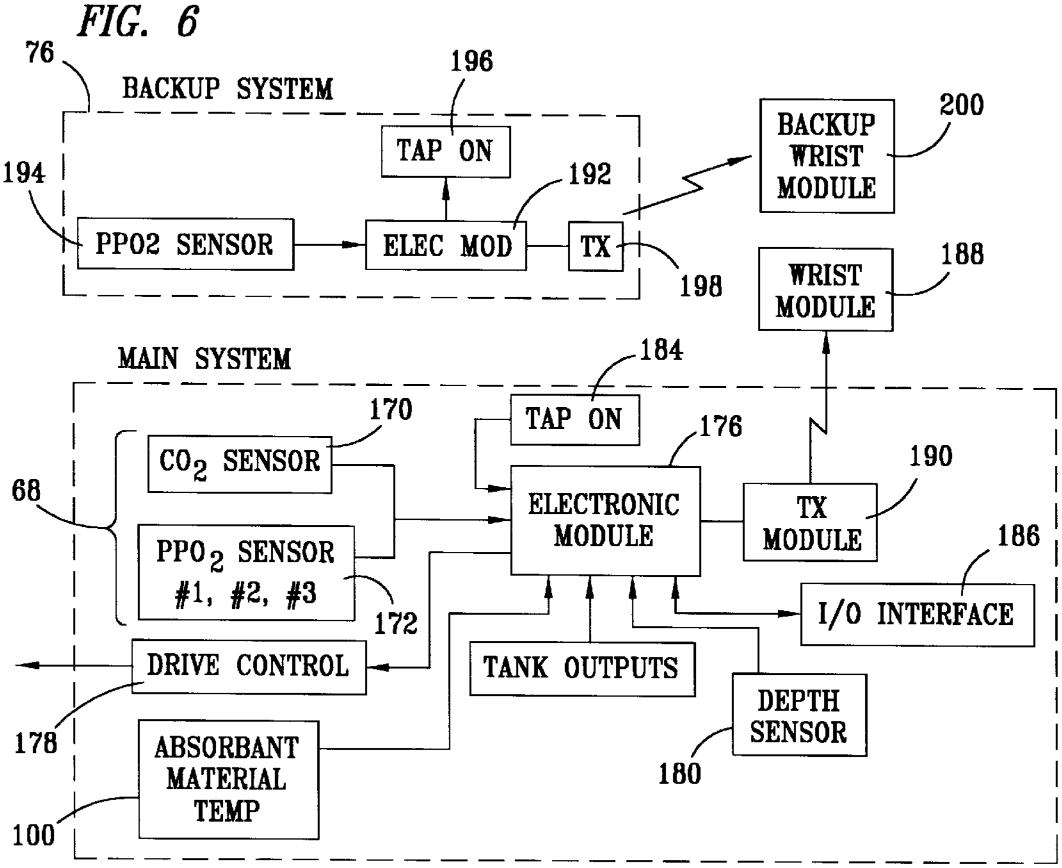
FIG. 6 illustrates a block diagram of the electronics control system.

Referring now to FIG. 6, there is illustrated a block diagram of the electronic and control portion 182 of the system. In general, the sensor block 68 is comprised of a $CO_2$ sensor 170 and a plurality of $PPO_2$ sensors 172, there being three utilized in the present invention. The $C_2$ sensor is bio-chemical $CO_2$ detector with reversible di-color changing indicator. This type of detector, well known in the art, is monitored and utilized to calculate the life of the absorbent 112 (shown in FIG. 2) or any failure in the various valves 34 and 38 (shown in FIG. 1). The $PPO_2$ sensors 172 are each operable to independently monitor the $O_2$ content of the loop to provide readings on what the diver is actually breathing. The $PPO_2$ sensors can utilize galvanic fuel cells of the type R17 manufactured by Teledene for the cells, but any type of sensor could be substituted. The reason for utilizing three cells is that one cell may not provide accurate readings. Therefore, the system can use a "voting" technique, wherein all three $PPO_2$ cells will read the $O_2$ levels and the two with the closest will be selected. This enhances reliability. The output of the sensors 170 and 172 are input to an electronic module, which contains the CPU 120 and is included within the electronics section 66 (shown in FIG. 2). This electronic module 66 is operable to generate a drive control signal to activate a drive control device 178 that is operable to generate the control signals for the stepper drive motor 146 (shown in FIG. 3). There are also provided various outputs from the tanks to provide the pressure levels at the tanks, these being conventional. Depth sensors 180 are also provided to give the depth of the unit. The absorbent material temperature strip 100 is also input to the electronic module 176. The electronic module 176 is activatable with a tap-on circuit 184. Tap-on circuit 184 is a piezoelectric transducer which, when stressed, generates an output. This output is sensed by the electronic module 66 and the information utilized. By tapping on this system and requiring a predetermined number of taps, this will provide an indication that the user wants to turn the system on. Inadvertent jolts or stresses of the piezoelectric transducer will not cause the system to turn on. Rather, there must be a sequence of rapid, hard taps. The electronic module 176 is also operable to interface with the exterior through an I/O interface 186 to allow programming and data transfer. This is a hard wire interface, but it can be a wireless interface also.

In order to allow the electronic module 176 to interface with a wrist module 188, a transmit module 190 is provided in association with electronic module 176. This transmit module 190 allows a low frequency carrier to be generated on which data is modulated. This is transmitted to the wrist module 188, which has a display associated therewith. Alternatively, a head mounted display unit could be utilized for this function.

As described above, a backup system 76 is provided that is disposed within the inhalant counterlung 18. This backup system 76 has associated therewith an electronic module 192, which interfaces with a $PPO_2$ sensor 194, this $PPO_2$ sensor 194 identical to the $PPO_2$ sensor 172, but entirely separate therefrom, such that it provides a redundant capability. A tap-on device 196, similar to the tap-on device 184, is provided for activating the system 76. The transmit module 198 allows the electronic module 192 to communicate with a separate backup wrist module 200. The backup system 76 with the backup wrist module 200 is a dive computer with the addition of the $PPO_2$ and $CO_2$ sensors. Therefore, the diver can utilize the backup system 76 to measure the $PPO_2$ level and transmit it to the backup wrist module 200 for display thereof. This backup system does not provide any control functions and is battery driven separate from that of the main system. It is a portable system that can maintain a personal log of the diver tissue saturation, etc. In the "bail-out" mode, the back-up system will act as a "standard" dive computer operating on the last known parameters.

Figure 7:
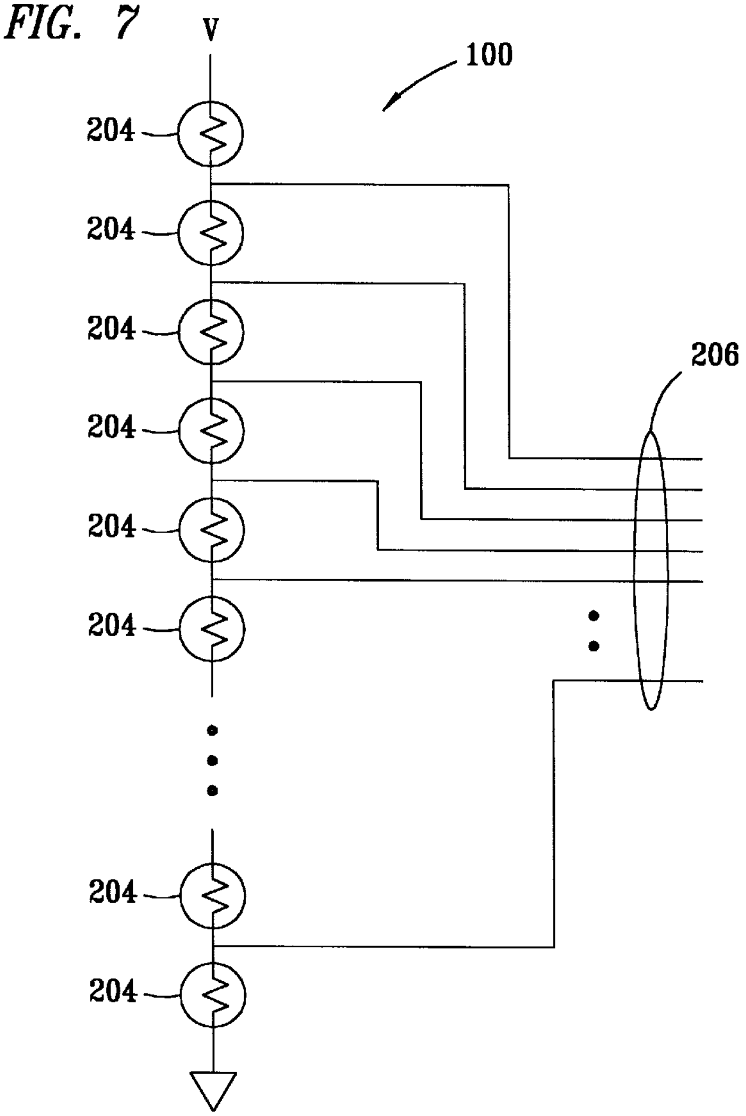
FIG. 7 illustrates a schematic diagram of the distributed temperature monitor.

Referring now to FIG. 7, there is illustrated a schematic diagram of the temperature sensor 100. The temperature sensor 100 is realized with a plurality of series connected thermistors 204. The thermistors 204 are connected in series between a voltage V and ground and are physically distributed along the length of the canister 10 on the outside walls thereof (shown in FIG. 2). The thermistors are disposed approximately 3 millimeters from the exterior wall of the inner canister 14 (shown in FIG. 2). A plurality of taps 206 are taken off all the thermistors 204, such that the voltage along the series connected thermistors 204 can be determined. With the use of these tapped voltages, the various resistances can be determined. Although illustrated as being connected to a voltage V, it could be connected to a constant current source.

Figure 8:
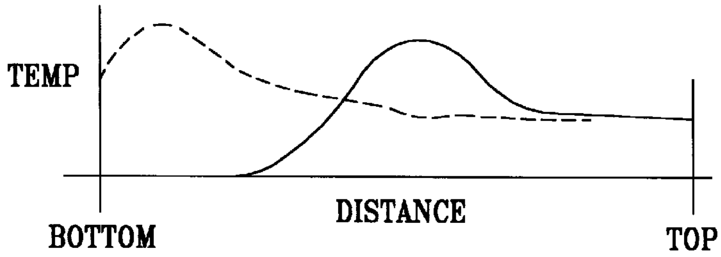
FIG. 8 illustrates a plot of temperature along the length of the canister during operation thereof.

Referring now to FIG. 8, there is illustrated a plot of temperature versus distance as determined along the length of the absorbent material 112 (shown in FIG. 2). The absorbent material 112 (shown in FIG. 2) has a characteristic that causes it to exhibit a localized heating along the length thereof. This localized heating occurs at a particular point, "the Flame Front," depending upon the amount of use of the absorbent material 112 (shown in FIG. 2). When it is new, the localized heat occurs at the bottom, as indicated by a dotted line. However, as it gets older, an increase in the heat level will be seen at another portion with the portion preceding being substantially cold, as it is used up. The portion at the top will be cooler than that at the localized region. Therefore, by looking at this temperature profile, a general idea of the life of the absorbent material 112 (shown in FIG. 2) can be determined. This information is calculated from the taps 206 (shown in FIG. 7) and then transmitted to the wrist module 188 (shown in FIG. 6) for display to the diver.

Figure 9:
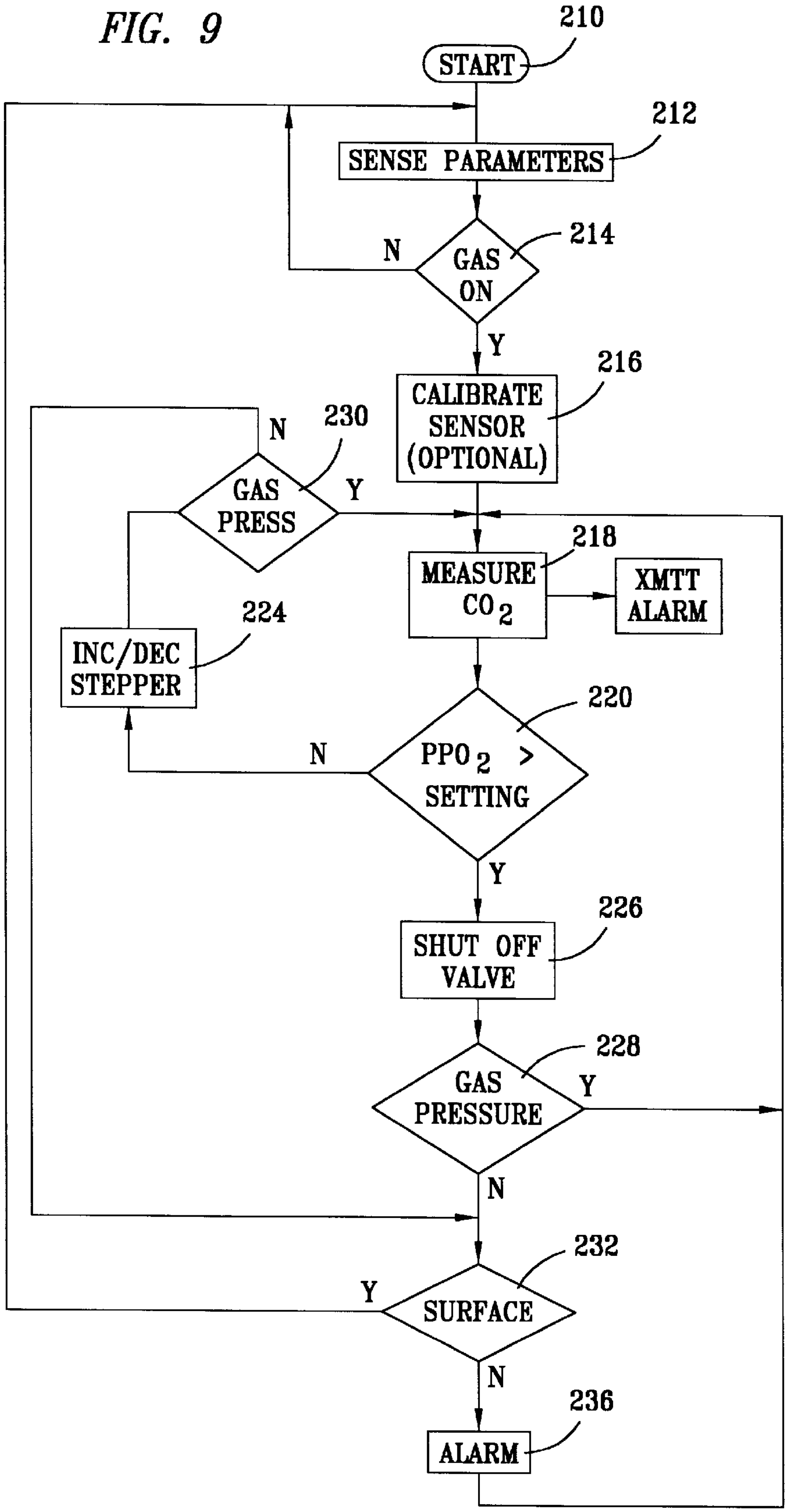
FIG. 9 illustrates a flow chart for the overall operation of the system.

Referring now to FIG. 9, there is illustrated a flow chart depicting the overall operation of the system. The program is initiated at a start block 210 and then proceeds to a function block 212 wherein the parameters are sensed. The program then flows to a decision block 214 to determine if the gas is on. This is determined by sensing the pressure at the gas tanks. If not, the program will flow back around an "N" path to the input of the function block 212. This will continue until the pressure of the gas has been sensed. At this point, the program will then flow along the "Y" path to a function block 216, wherein a calibration operation can be formed. This is typically something that is done at the surface and is a predetermined routine that is performed by the system. However, this is not required. After the optional calibration step, the program will flow to a function block 218, wherein the $CO_2$ level is measured. If the $CO_2$ level is excessive, this will generate an alarm. However, an excess level of $CO_2$ will not cause the system to operate in a different manner, as this is not connected to the overall feedback for controlling the valve 46 (shown in FIGS. 1 and 3). After the $CO_2$ level has been measured, the program flows to a decision block 220, wherein the $PPO_2$ level is measured and compared with a predetermined level. When the $PPO_2$ level is less than the determined setting, the system will perform two steps, either increment or decrement the stepping motor 146 (shown in FIG. 3). When the $PPO_2$ level is relatively low upon initiation of the system, or when the diluent level is increased to flush the system, then the stepping motor 146 (shown in FIG. 3) will be incremented in a positive manner to open the valve 46. This will increase the flow rate of $O_2$. However, when the $PPO_2$ level approaches the predetermined setting, the stepping motor 146 will be decremented to decrease the flow rate such that, when the $PPO_2$ level is equal to the predetermined setting, the valve 46 (shown in FIGS. 1 and 3) will be at the approximate level, such that it will not overshoot the predetermined setting. Additionally, the system can compensate for the rate of decrementing or the rate of incrementing as a function of temperature and depth, which is facilitated along the "N" path from decision block 220 through an increment/decrement function block 224. The system will then return to the input of the function block 218 until the stepping motor 146 (shown in FIG. 3) is incremented to the appropriate level.

Whenever the $PPO_2$ level exceeds the setting, the program will flow from the decision block 220 to a function block 226 to shut off the valve 46 (shown in FIGS. 1 and 3) to inhibit flow therethrough. The program will then flow to a decision block 228 to determine if there is gas pressure in the tanks. If so, the program will flow along a "Y" path back to the input of the function block 218. Additionally, a decision block 230 disposed between function block 224 and function block 218 to determine if there is gas pressure in the system.

When gas pressure falls, the program will flow from decision block 228 or decision block 230 along the "N" paths thereof to a function block 232 to determine if the system is at the surface. If it is at the surface, it will recognize from the pressure that an alarm need not needed. If this is the case, the program will flow along the "Y" path back to the input of function block 212 to again reinitiate the system. However, if the system is not at the surface and the gas pressure has fallen below an acceptable level, the program will flow along the "N" path to a function block 236 to set an alarm and then back to the input of function block 218. This alarm will alert the diver to the fact that pressure is dangerously low.

Figure 10:
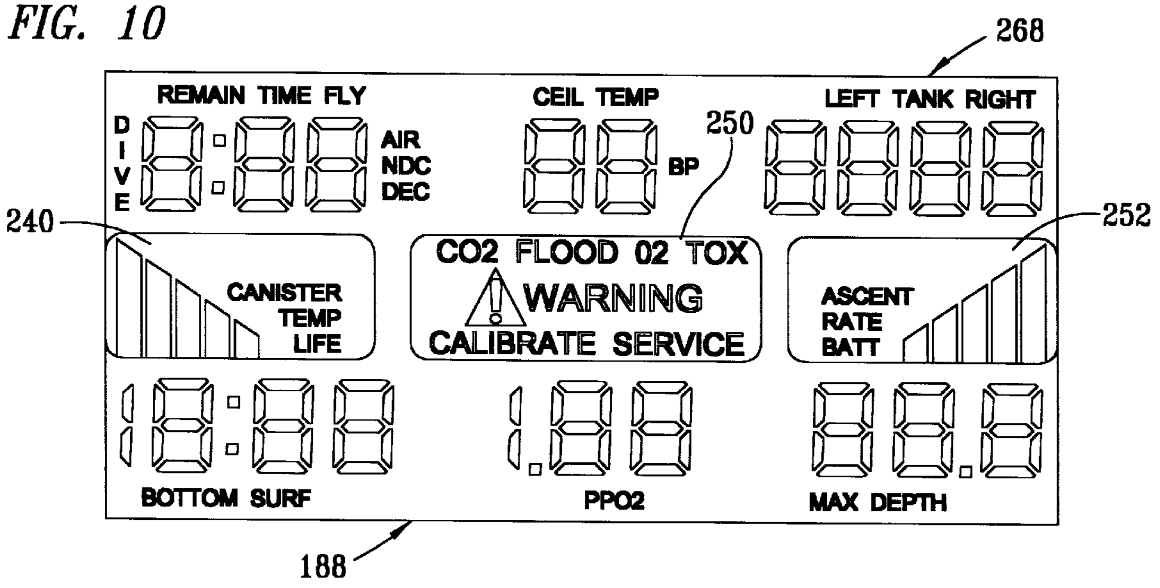
FIG. 10 illustrates a display for a wrist unit.

Referring now to FIG. 10, there is illustrated a top view of a display 268 in the wrist module 188. The display 268 has a number of different fields. On the top there is provided the amount of time that is remaining for the dive and the ceiling for the first decompression stop. The temperature is also provided in addition to the pressure in the tank on the upper right side of the display 268. This alternates between the left tank and the right tank. On the lower edge of the display 268, depth is provided, in addition to, in the center thereof, the $PPO_2$ level. The $PPO_2$ level is displayed as both $PPO_2$ level and the percent $PPO_2$. The display 268 provides for two methods of operation or two displays, a main display and an alternate display. The alternate display can be accessed merely by tapping on the system after it has been activated, it being understood that activation of the wrist unit 188 is achieved by tapping on the system. Once activated, additional tapping a predetermined number of times at a predetermined rate will cause the display 268 to switch from the primary display to the secondary display. In the secondary display, the gas $O_2$ percentage is displayed. This provides a mode wherein the diver will have access to both types of information. However, the $PPO_2$ and the percentage $O_2$ could be displayed on the primary display.

In addition to the normal display aspects, there are provided three areas in the center of the display 268, an area 240, an area 250, and an area 252. The area 240 is associated with the canister life. This is the temperature calculation that was provided by the temperature strip 100. This illustrates the percentage of the canister 14 (shown in FIGS. 1 and 2) that is used up, this being derived primarily from the temperature monitor 100. The region 250 provides the alarm systems. The alarm system indicates if the $CO_2$ level is too high, if the $O_2$ is too high, and also if there is a flood condition, wherein the water detector 12 (shown in FIG. 2) has detected a level of salt water. The region 252 is provided to indicate the ascent rate or the battery level.

Figure 11:
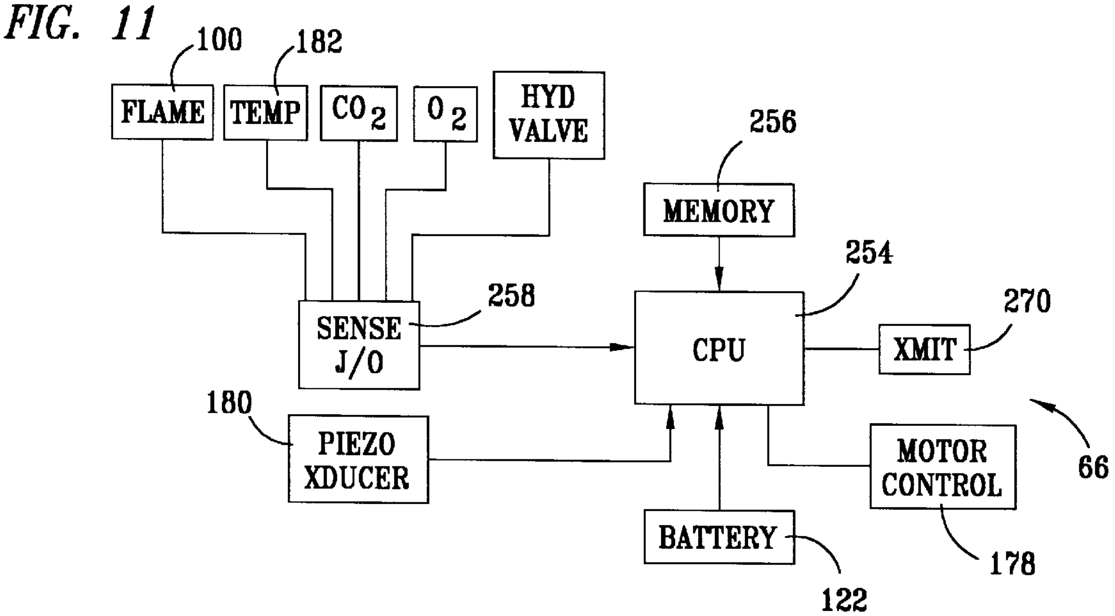
FIG. 11 illustrates an overall block diagram of the electronic module on the tanks.

Referring now to FIG. 11, there is illustrated a general block diagram of the electronic module 66. The electronic module 66 is generally comprised of a microprocessor-based CPU 254, which has associated therewith a memory 256 and the battery 122. The CPU 254 controls the motor or drive control 178 and also has associated therewith a piezoelectric transducer 180. The sensing operation is achieved through a sensing I/O 258, which is operable to sense the temperature monitor (flame 100), the internal temperature sensing element 182, the $CO_2$ and $O_2$ levels, and also the hydrostatic pressure on the valves of the tanks. This is all operable to interface with the transmitter 270, which transmitter 270 provides the ability to modulate the carrier and transmit this to the transmit module 190 (shown in FIG. 6) for transmission to the wrist module 180 (shown in FIG. 6) with a wireless communication link.

Figure 12:
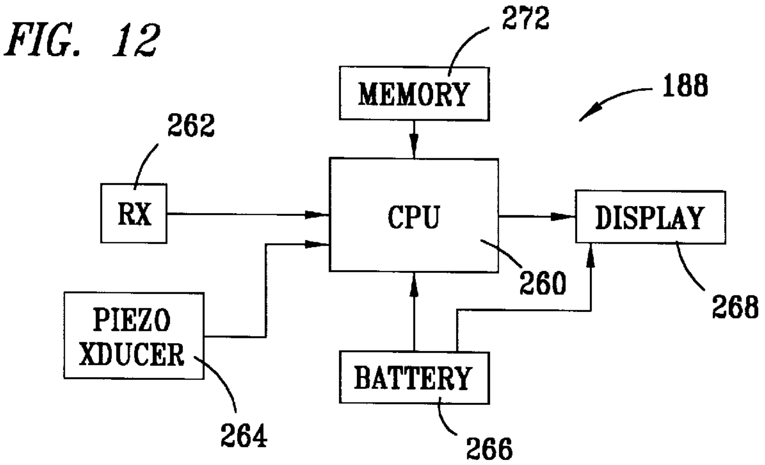
FIG. 12 illustrates a block diagram of the wrist unit.

Referring now to FIG. 12, there is illustrated a block diagram of the wrist module 188. The wrist module 188 is generally comprised of a microprocessor-based CPU 260, which is operable to interface with a receiver 262, which is operable to receive the information from the transmit module 190 (shown in FIG. 6). A separate piezoelectric transducer 264 is provided which comprises a tap-on device, similar to tap-on device 196 and tap-on device 184 (shown in FIG. 6). This is typically mounted adjacent the housing, it being understood that the entire wrist module 188 is housed in a waterproof housing. An internal battery 266 is provided for providing power. This wrist module 188 also includes a display 268, which is described above with respect to FIG. 10. A memory 272 is provided for storing data and for storing program instructions. In the event of a failure, the wrist unit 188 will utilize the last recorded data and switch to a standard dive computer operation mode providing abort/decompression profiles based upon that data and any preprogrammed abort plans and default settings.

The system operates in multiple modes and there being three primary modes, mode 1, mode 2 and mode 3. Mode 1 is a semi-closed circuit operation wherein a constant percentage of $O_2$ is provided to the diver. Typically, the percentage would be set around 40% $O_2$. Therefore, as the diver descends and the depth increases, the percentage of $O_2$ stays the same in the gas, even though the pressure of the gas increases. The diver has provided on the display 268 the option of selecting either the $PPO_2$ display or the $O_2$ percentage display. By tapping the wrist unit 188, the diver can alternate between these two displays. Of course, in a constant $O_2$ environment, the $PPO_2$ will change based upon the workload of the diver and the depth. Since this is a semi-closed circuit, this will require the valve 60 (shown in FIG. 1) to allow excess gas to escape. This valve 60 (shown in FIG. 1) is set at a predetermined pressure and, when the exhalent counterlung 20 (shown in FIG. 1) reaches a certain pressure, this will allow gas to "vent".

In the second mode, mode 2, this is also a semi-closed constant $PPO_2$ system wherein pure $O_2$ is not injected into the system. In this type of a system, the gas that is injected into the system is either obtained from a diluent gas source or some other gas source that has more than pure $O_2$ gas contained therein. Therefore, there will be additional gas that will neither be "metabolized" nor removed by the canister 10 (shown in FIG. 1) and, as such, it must be vented through the valve 60 (shown in FIG. 1).

In the semi-closed circuit modes, the system is operable to calculate the various dive parameters, such as tissue saturation, etc., based upon known flow rates known gas mix and depth. These are displayed to the diver. In addition, this allows the diver to perform a calibration check of suspect readings.

In the third mode, the fully closed circuit mode as described hereinabove, a constant $PPO_2$ level is provided with only the amount of oxygen necessary to replace the metabolized oxygen injected into the inhalant counterlung 18. All three modes can be selected with the dive computer basically monitoring and controlling whether the system is in a constant $PPO_2$ mode or in a constant $O_2$ percentage mode, this merely requiring there be a $PPO_2$ sensor and a gas metering device, such as the valve 46 (shown in FIG. 1). The percentage of gas is readily calculated from the PPO2 value. The valve 46 (shown in FIG. 1) provides the ability to provide a constant velocity flow of air at any level and, even provide a positive shut-off for the gas and prevent any $O_2$ being input to the inhalant counterlung 18 (shown in FIG. 1).

Figure 13:
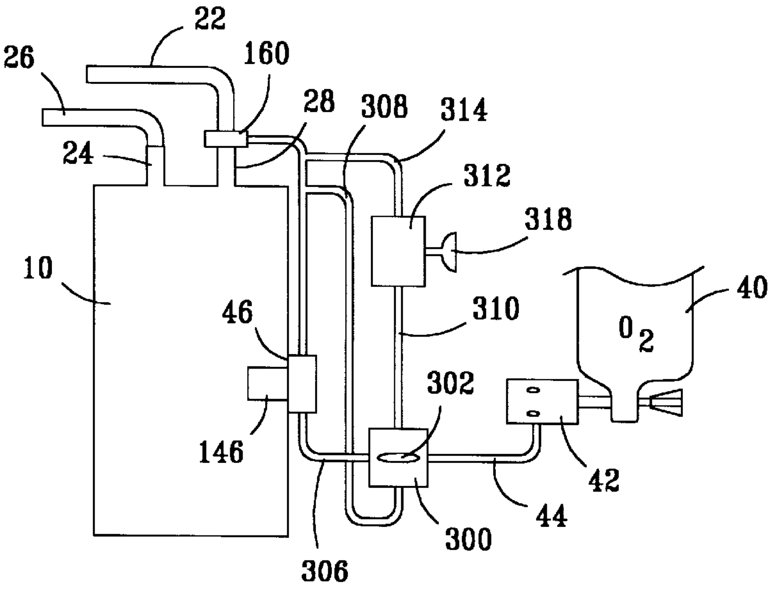
FIG. 13 illustrates a schematic diagram of an alternative embodiment for controlling the flow of oxygen from a supply bottle to an inlet and a supply hose.

Referring now to FIG. 13, there is illustrated an alternate embodiment for allowing control of the oxygen that is received from the bottle 40 and regulator 42 to the inlet to hose 22. The hose 44 that is connected to the regulator 42 is connected to a 4-way ball valve 300 which is manually positioned with a control 302 that allows the air to be directed to one of three outputs. A first output is connected to a hose 306 that is input to the valve 46. A second output is connected through a hose 308 to the inlet to the hose 22. A third outlet is connected through a hose 310 to a manual valve 312. The outlet of the manual valve 312 is connected through a hose 314 to the inlet to the hose 22. In operation, the first mode will be selected with the 4-way valve 300 by connecting the hose 44 to the hose 306 and allowing the step-up motor 146 to operate the system, this being the automatic mode. The second mode is a manual mass flow control mode which is facilitated with the selection of the hose 310 for input to the valve 312. The valve 312 is a manually controlled mass flow controller, essentially a needle valve similar to the construction of the valve 46. However, this needle valve is controlled with a control knob 318 that allows the diver to manually select the flow rate. The third mode is facilitated by selecting the hose 308 for completely bypassing both the valve 46 and the valve 312 and the gas will be injected directly into the hose 22. In a fourth mode, the valve 302 can be placed in a mode where it shuts off the gas completely.

In summary, there has been provided a breathing apparatus that operates in multiple modes. The breathing apparatus is a re-breather having first and second counterlungs, one for inhalant and one for exhalant. A mouthpiece bridges the two counterlungs, such that gas flows from the inhalant counterlung to the exhalant counterlung through the mouthpiece. The inhalant counterlung receives gas from a scrubber canister, the exhalant counterlung outputs gas to the canister, the canister removes carbon dioxide from the recycled gas. An oxygen tank is provided for introducing either oxygen or an oxygen-rich gas into the inhalant counterlung through a constant flow variable valve. The constant flow variable valve has the flow rate thereof selected with a stepper motor, which flow rate is variably selected even during a dive. This is a closed circuit system and is controlled by a $PPO_2$ sensor disposed in the inhalant counterlung. A drive control system is provided for varying the flow rate of the oxygen to the inhalant counterlung as a function of the $PPO_2$ level, maintaining the $PPO_2$ level at a substantially constant level.

Although the preferred embodiment has been described in detail, it should be understood that various changes, substitutions and alterations can be made therein without departing from the spirit and scope of the invention as defined by the appended claims.

What is claimed is:

1. A breathing apparatus, comprising:

an inhalant counterlung having an inlet hose for receiving $CO_2$ -depleted gas and an outlet hose for outputting breathable gas;

a breathing mouthpiece for allowing a user to breathe, said breathing mouthpiece having an inlet connected through a first one-way valve to said outlet hose of said inhalant counterlung for receiving inhaled gas, said mouthpiece having an outlet for passing through a second one-way valve, to expel exhaled gas from the user;

a $CO_2$ scrubber canister for receiving the output of said mouthpiece through said second one-way valve, removing $CO_2$ from said exhaled gas and outputting $CO_2$-depleted gas to the input of said inhalant counterlung;

an $O_2$ source;

a variable flow rate valve connected between said $O_2$ source and the interior of said inhalant counterlung, and operable to set the flow rate at a desired level;

a $PPO_2$ sensor for sensing the partial pressure of $O_2$ in the inhaled gas; and a driver control circuit which includes a stepper motor for variably actuating said variable flow rate valve for varying the flow rate of said variable flow rate valve as a function of said $PPO_2$ level to maintain said $PPO_2$ level in the inhaled gas at a substantially constant and predetermined level.

2. The breathing apparatus of claim 1 and further comprising an exhalant counterlung disposed between said mouthpiece and the input of said $CO_2$ scrubber/canister.

3. The breathing apparatus of claim 1 and further comprising a diluent tank and a diluent valve connected between said diluent tank and the interior of said inhalant counterlung, said diluent valve allowing the user to manually increase the volume in said inhalant counterlung.

4. The breathing apparatus of claim 3, wherein said diluent valve is operable to increase the pressure within said inhalant counterlung as a result of an increase in pressure exterior to said inhalant counterlung.

5. The breathing apparatus of claim 1, wherein said variable valve is interfaced with the outlet of said $CO_2$ scrubber canister, wherein the outlet of said $CO_2$ scrubber canister is connected through a flexible hose to the inlet of said inhalant counterlung.

6. The breathing apparatus of claim 1, wherein said variable flow rate valve comprises a needle valve, which has a needle member with a tapered surface for being disposed through an orifice having vertical walls, said needle member advanced with a rotational motion about the axis of said needle member, said needle valve providing a constant flow rate and further comprising a regulator for regulating the pressure on the inlet side of said needle valve from the pressure within said $O_2$ source to provide a constant velocity through said orifice with said needle disposed therein.

7. The breathing apparatus of claim 6, wherein said driver control circuit comprises:

said stepper motor wherein said stepper motor variably actuates said needle valve by positioning said needle in said needle valve in incremental steps; and a control system for generating and incrementing a control signal for controlling said stepper motor to increment or decrement the rotation of said needle in said needle valve.

8. The breathing apparatus of claim 1, wherein said variable flow rate valve is infinitely variable at substantially any setting, providing a constant velocity at substantially all flow rates in the operating range of said valve.

9. The breathing apparatus of claim 1, wherein said variable flow rate valve is operable to be shut off, wherein said shut off condition is a positive shut off.

10. The breathing apparatus of claim 1, and further comprising a backup $PPO_2$ sensor for sensing the partial pressure of $O_2$ in said inhaled gas that operates independent of said $PPO_2$sensor, and a backup system monitoring said $PPO_2$ level independent of said $PPO_2$ sensor and the driver control circuit.

11. The breathing apparatus of claim 10, and further comprising a bypass valve for bypassing said variable flow rate valve independent of said driver control circuit for allowing manual setting of the $O_2$ rate from said $O_2$ source to the interior of said inhalant counterlung.

12. The breathing apparatus of claim 11, wherein said bypass valve comprises a variable flow rate valve that is manually operated.

13. The breathing apparatus of claim 1, and further comprising a manual bypass valve for bypassing said variable flow rate valve and not controlled by said driver control circuit, said manual valve operable to be controlled by the user.

14. The breathing apparatus of claim 13, wherein said manual bypass valve comprises a variable flow rate valve that is manually operated to set the flow rate therethrough.

15. The breathing apparatus of claim 13, wherein said manual bypass valve is operable to directly inject the full flow rate from said $O_2$ source into said inhalant counterlung.

16. The breathing apparatus of claim 1, wherein said $CO_2$ scrubber canister comprises a canister containing a $CO_2$ absorbent material, which absorbent material exhibits localized heating along the length of said canister, which localized heating area moves along the length thereof as said absorbent material is utilized.

17. The breathing apparatus of claim 16, and further comprising:

a distributed temperature probe for measuring the temperature at selected locations which are spaced apart along the length of said canister; and a temperature monitoring device for determining the approximate location relative to said spaced apart locations along the length of said canister of said localized heating as determined by said distributed temperature monitor, and converting said position to a canister life value and displaying said value on a display for viewing by the user.

18. A breathing apparatus, comprising:

an inhalant counterlung having an inlet hose for receiving $CO_2$ -depleted gas and an outlet hose for outputting breathable gas;

a breathing mouthpiece for allowing a user to breathe, said breathing mouthpiece having an inlet connected through a first one-way valve to said outlet hose of said inhalant counterlung for receiving inhaled gas, said mouthpiece having an outlet for passing through a second one-way valve, to expel exhaled gas from the user;

a $CO_2$ scrubber canister for receiving the output of said mouthpiece through said second one-way valve, removing $CO_2$ from said exhaled gas and outputting $CO_2$-depleted gas to the input of said inhalant counterlung, an $O_2$ source;

a variable flow rate valve connected between said $O_2$ source and the interior of said inhalant counterlung, and operable to set the flow rate at a desired constant velocity level;

a $PPO_2$ sensor for sensing the partial pressure of $O_2$ in the inhaled gas;

a driver control circuit which includes a stepper motor for variably actuating said variable flow rate valve for varying the flow rate of said variable flow rate valve as a function of the percentage of oxygen in the inhaled gas;

a venting valve for maintaining the volume of gas in the breathing apparatus below a predetermined level;

a distributed temperature monitor disposed along the length of said canister, and having spaced apart localized sensor regions disposed proximate to relative positions along the length of the absorbent material; and a computational device for determining from said distributed temperature monitor the relative position of the localized heating and converting said localized heating position to a lifetime value for the absorbent material.

19. The breathing apparatus of claim 18, and further comprising a display for displaying in alternate displays the percentage $O_2$ level and said $PPO_2$ level.

20. The breathing apparatus of claim 18, and further comprising a display for displaying simultaneously the percentage $O_2$ level and said $PPO_2$ level.

* * * * *